(12) United States Patent
Laing

(10) Patent No.: US 9,913,479 B2
(45) Date of Patent: Mar. 13, 2018

(54) RODENT REPELLANT SYSTEM

(71) Applicant: David Laing, Hamilton, NJ (US)

(72) Inventor: David Laing, Hamilton, NJ (US)

(*) Notice: Subject to any disclaimer, the term of this patent is extended or adjusted under 35 U.S.C. 154(b) by 242 days.

(21) Appl. No.: 15/050,148

(22) Filed: Feb. 22, 2016

(65) Prior Publication Data

US 2017/0020142 A1    Jan. 26, 2017

Related U.S. Application Data

(60) Provisional application No. 62/118,899, filed on Feb. 20, 2015.

(51) Int. Cl.
| | | |
|---|---|---|
| *A61K 36/00* | (2006.01) | |
| *A01N 65/22* | (2009.01) | |
| *A01M 13/00* | (2006.01) | |
| *A01M 3/00* | (2006.01) | |
| *B08B 1/00* | (2006.01) | |
| *B05B 11/00* | (2006.01) | |

(52) U.S. Cl.
CPC .............. *A01N 65/22* (2013.01); *A01M 3/00* (2013.01); *A01M 13/00* (2013.01); *B05B 11/3052* (2013.01); *B08B 1/006* (2013.01)

(58) Field of Classification Search
CPC ....................................................... A61K 36/00
USPC ....................................................... 424/725
See application file for complete search history.

(56) References Cited

FOREIGN PATENT DOCUMENTS

JP            49030525 A    *    3/1974

* cited by examiner

*Primary Examiner* — Michael V Meller
(74) *Attorney, Agent, or Firm* — Ruth Eure

(57) ABSTRACT

A rodent repellent system for repelling rodents from an area is provided. The rodent repellent system comprises a dispersing mechanism and an amount of natural peppermint oil in fluid communication with the dispersing mechanism. The natural peppermint oil has a peppermint aroma with the dispersing mechanism releasing the peppermint aroma into the area.

1 Claim, 8 Drawing Sheets

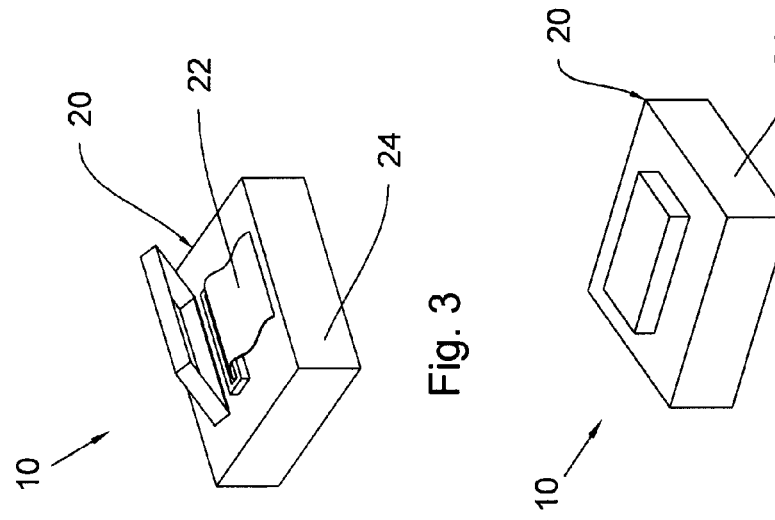
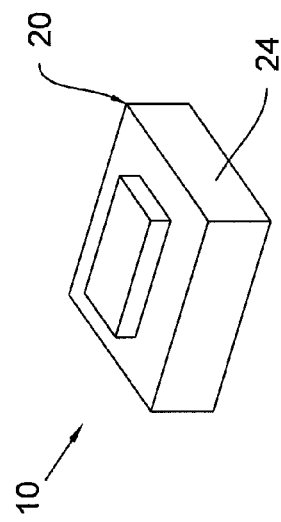
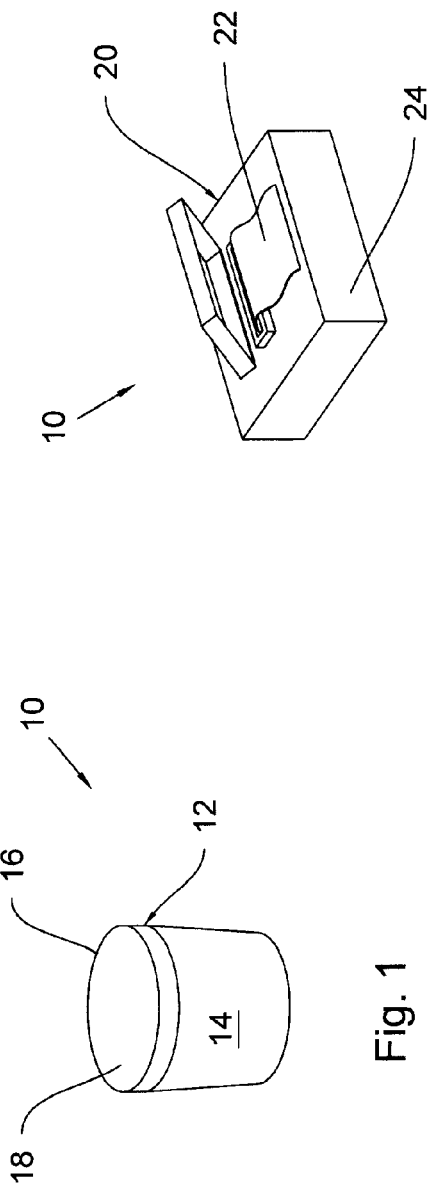
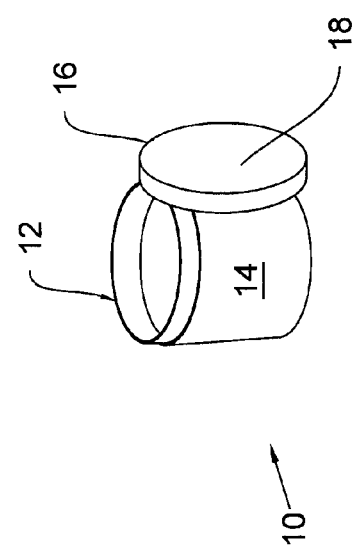

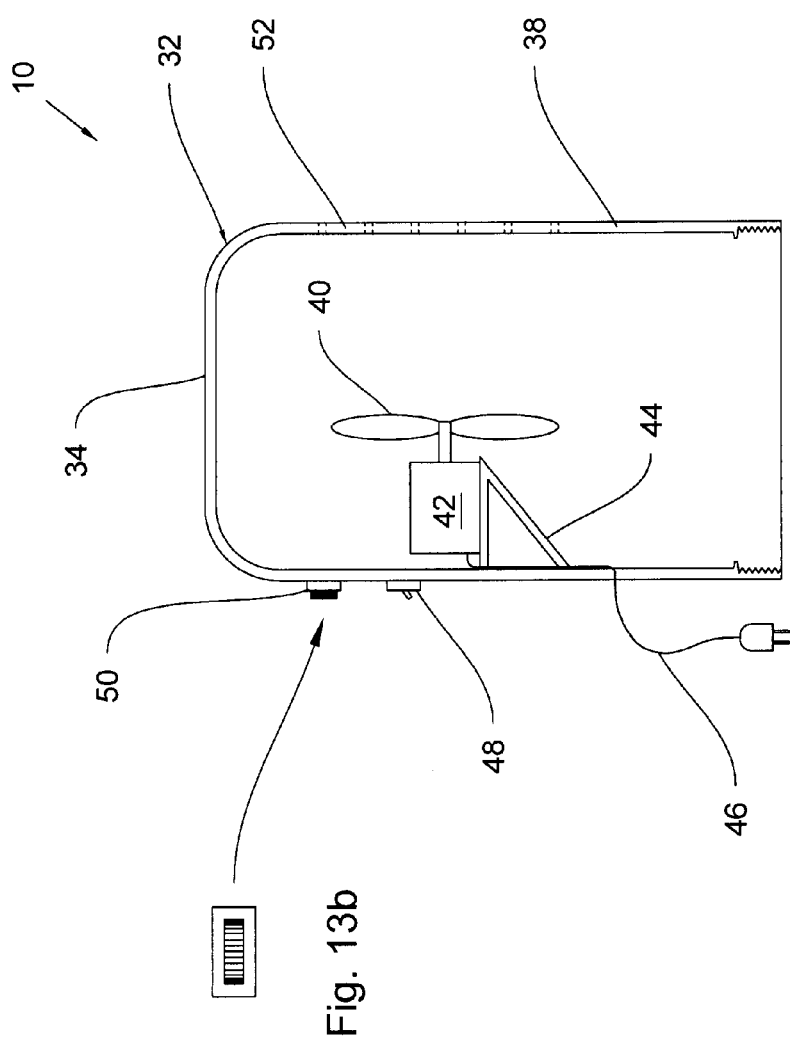

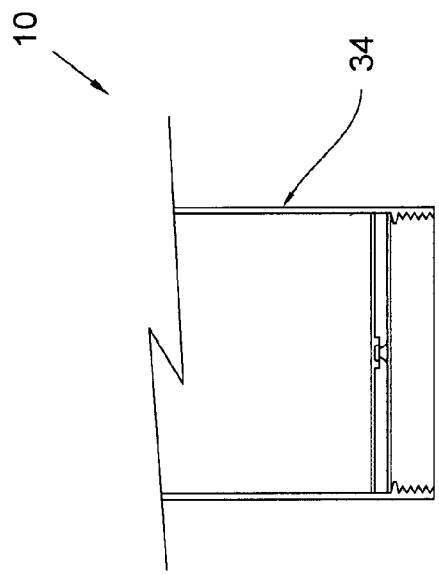
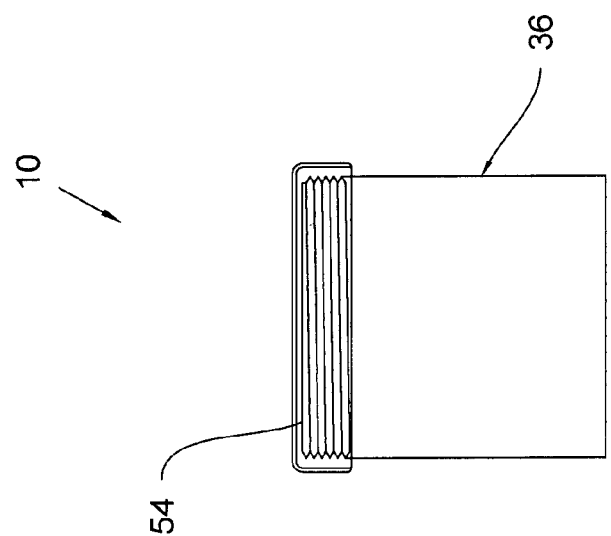

RODENT REPELLANT SYSTEM

CLAIM OF PRIORITY

This patent application claims priority under 35 USC 119 (e) (1) from U.S. Provisional Patent Application Ser. No. 62/118,899 filed Feb. 20, 2015, of common inventorship herewith entitled, "Mouse-A-Way," which is incorporated herein by reference as though the same were set forth in its entirety.

FIELD OF THE INVENTION

The present invention pertains to the field of rodent populations, and more specifically to the field of rodent repellents.

BACKGROUND OF THE INVENTION

Homeowners are always on the lookout for the next best product, the one thing that resolves a problem perfectly. They're interested in convenient and quick fixes that are dependably and responsibly usable without harming others or the environment. Natural foods, recycling, alternative fuel sources and biodegradable materials are becoming a way of life for many individuals. Many people are choosing to eat healthier foods over convenient fast foods, more electric and hybrid cars are on highways, more recycle bins are in kitchens and clothing lines are resurging as a clothes drying method. Many individuals are looking for an appealingly scented pest repellant that permits unwanted guests to scurry away and live their lives elsewhere.

The prior art has put forth several designs for rodent repellents. Among these are:

US Pat. No. 2012/0003336 to Jonathan P. Del Grande describes a rodent and insect repellent system that effectively deters or repels rodents, squirrels, small animals and crawling insects from entering vehicles such as cars, trucks, motor homes, trailers, tractors and recreational vehicles. The invention is a process in which an application of a non drip oily coating is applied to the entire undercarriage and engine compartment of a vehicle. The coating prevents rodents, squirrels, small animals and crawling insects from traveling across areas coated. This coating stays wet and slippery to the touch without dripping or drying out. The coating is scented with natural essential oils which overwhelm a rodent's acute sense of smell and drive them away from the vehicle.

U.S. Pat. No. 5,556,881 to Margaret R. Grahn Marisi describes an insect repellent and insecticide formulation for repelling and killing insects. The formulation includes a volume of water and essential ingredients of acetic acid and a limonene, particularly a mint extract.

U.S. Pat. No. 1,871,949 to Henry T. Bottrell describes a rodent repellant and insecticidal composition including ingredients from which rodents and insects will retreat, ingredients which will destroy insects, and an ingredient with fumes that will drive insects out of concealment and into contact with the destructive ingredients of the compound. These ingredients are combined so that the same will adhere to one another and will also adhere to the material treated by the mixture. The mixture of the materials is manufactured in concentrated form so that it consists in its novel features hereinafter despite atmospheric conditions. The mixture container is readily transported or stored in relatively small space. The mixture includes oil of peppermint, sodium benzoate, sulphonethylmethane, animal glue, eight percent wood alcohol and water.

None of these prior art references describe the present invention.

SUMMARY OF THE INVENTION

It is an object of the present invention to provide peppermint scented, oil based air fresheners and surface wipes that deter mice from entering homes and other areas.

The present invention is a rodent repellent system for repelling rodents from an area. The rodent repellent system comprises a dispersing mechanism and an amount of natural peppermint oil in fluid communication with the dispersing mechanism. The natural peppermint oil has a peppermint aroma with the dispersing mechanism releasing the peppermint aroma into the area.

In addition, the present invention is a method for repelling rodents from an area. The method comprises providing a dispersing mechanism, fluidly communicating an amount of natural peppermint oil with the dispersing mechanism, and releasing a peppermint aroma into the area.

BRIEF DESCRIPTION OF THE DRAWINGS

FIG. 1 is a perspective view illustrating a gel based air freshener of the rodent repellent system, constructed in accordance with the present invention with a top cover twistable to expose open holes;

FIG. 2 is another perspective view illustrating the gel based air freshener of the rodent repellent system of FIG. 1, constructed in accordance with the present invention with the top cover removed.

FIG. 3 is a perspective view illustrating a surface wipe embodiment of the rodent repellent system, constructed in accordance with the present invention, with an opened container lid exposing a wipe ready to be pulled out of a canister.

FIG. 4 is another perspective view illustrating the surface wipe embodiment of the rodent repellent system of FIG. 3, constructed in accordance with the present invention, with a tight lid closed over the canister's opening to preserve peppermint essence.

FIG. 13a is an elevational sectional side view illustrating the fan housing of the fan dispersing embodiment of the rodent repellent system of FIG. 12, constructed in accordance with the present invention.

FIG. 13b is a front view illustrating a speed control wheel of the fan dispersing embodiment of the rodent repellent system of FIG. 12, constructed in accordance with the present invention.

FIG. 14 is an elevational side view illustrating a concentrate housing of the fan dispersing apparatus embodiment of the rodent repellent system of FIG. 12, constructed in accordance with the present invention, with the concentrate housing being covered by a removable foil seal.

FIG. 15 is an elevational side view illustrating the fan housing of the fan dispersing apparatus embodiment of the rodent repellent system of FIG. 12, constructed in accordance with the present invention.

DETAILED DESCRIPTION OF THE INVENTION

Figure 6:
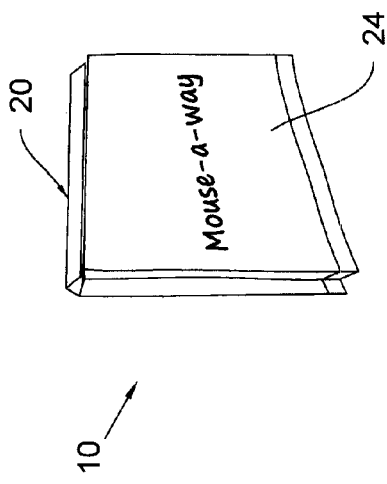
FIG. 6 is a perspective view illustrating still another embodiment of the surface wipe embodiment of the rodent repellent system, constructed in accordance with the present invention.
Figure 8:
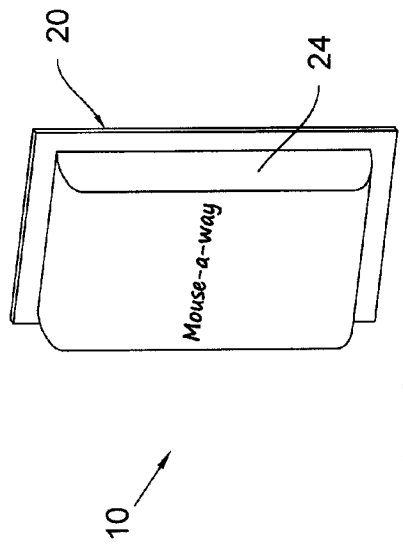
FIG. 8 is a perspective view illustrating still yet another embodiment of the surface wipe embodiment of the rodent repellent system, constructed in accordance with the present invention.
Figure 5:
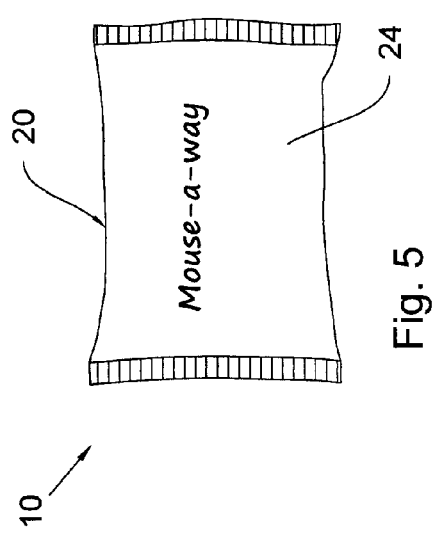
FIG. 5 is a perspective view illustrating another embodiment of the surface wipe embodiment of the rodent repellent system, constructed in accordance with the present invention, with a soft sided packaging and a resealable flap.
Figure 7:
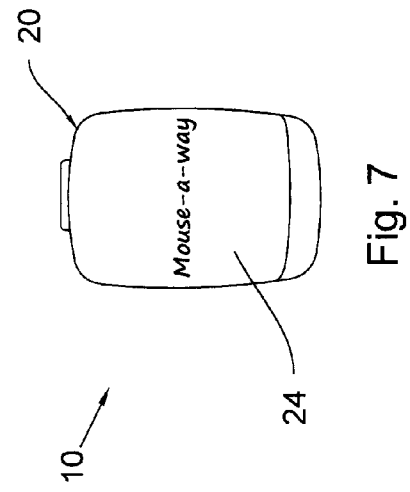
FIG. 7 is a perspective view illustrating yet another embodiment of the surface wipe embodiment of the rodent repellent system, constructed in accordance with the present invention.

The present invention, hereinafter referred to as a Rodent Repellent System, indicated generally at 10, is a line of pest repellants that uses peppermint oil instead of poison or other harmful chemicals. The Rodent Repellent System 10 line contains both oil based air fresheners and oil based surface wipes that repel rodents or mice using a wholly natural oil of peppermint. Peppermint oil contains no chemicals and effectively functions as a natural rodenticide by emitting a scent that repels any mouse or rodent from coming near it. Instead of killing rodents, endangering pets and loved ones, and possibly contaminating one's food, the Rodent Repellent System 10 relies on the scent of a natural and non harmful oil to scare rodents away.

The Rodent Repellent System 10 of the present invention comes in multiple embodiments. The first embodiment, as best illustrated in FIGS. 1 and 2, is a gel based air freshener 12. Short and cylindrical in shape, the Rodent Repellent System 10 gel based air freshener is contained in a preferably hard plastic container 14 with a removable top cover 16. When a user manually twists the top cover 16, small holes 18 are exposed in the top cover 16 of the container 14, allowing the scent of peppermint oil gel to waft out of the container 14 and throughout the immediate surroundings. The gel based air freshener 12 of the Rodent Repellent System 10 preferably measures approximately two and one half (2½") inches in height and approximately two and three quarter (2¾") inches in diameter although a larger or smaller gel based air freshener 12 is within the scope of the present invention. Depending the desires of the user, the user may place the gel based air freshener 12 discretely in faraway corners, behind a fridge, in a pantry or on a countertop.

As best illustrated in FIGS. 3-8, the second embodiment of the Rodent Repellent System 10 of the present invention is a surface wipe system 20 comprising a surface wipe 22 removable from a canister 24 which a user may use to apply a small amount of peppermint oil to a specific area. The surface wipes 22 can be stored in a variety of canisters 24 including, but not limited to, soft sided packaging and hard plastic cases. The soft sided packaging includes, but is not limited to, peel-reseal and semi-rigid canisters 24. In an embodiment of the soft sided packaging, the soft sided packaging includes a resealable flap with thirty (30) premoistened wipes that pull out individually or one at a time. The packaging can be a coated package with a foil lining although other types of packaging is within the scope of the present invention. The hard plastic canister 24 of the surface wipe system 20 embodiment preferably measures approximately four (4") inches long by two (2") inches wide although having different measurements are within the scope of the present invention.

In operation of the surface wipes 22 of the Rodent Repellent System 10 of the present invention, the user pulls one surface wipe 22 at a time and then wipes down a mouse's or other rodent's favorite hangout or entrance area to prevent the mouse and/or rodent returning. The surface wipes 22 are recommended for countertops and pantry shelves which contain items prone to mouse and/or rodent snooping.

As stated briefly above, the canisters 24 of the surface wipes system 20 of the Rodent Repellent System 10 of the present invention includes both soft sided and hard sided canisters 24, refills with a resealable label, dispenser softpacks with flip top lid, tubs, canisters, travel packs, individually packed sachets, and various pack and case counts.

Figure 11:
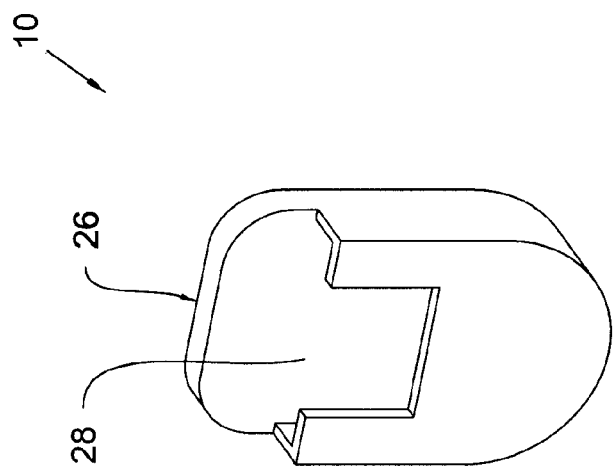
FIG. 11 is a perspective view illustrating the electrical air freshener embodiment of the rodent repellent system of FIG. 9, constructed in accordance with the present invention, with a recessed component for holding the refillable mats that contain the peppermint oil.
Figure 10:
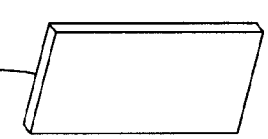
FIG. 10 is a perspective view illustrating a refillable mat for the electrical air freshener embodiment of the rodent repellent system of FIG. 9, constructed in accordance with the present invention.
Figure 9:
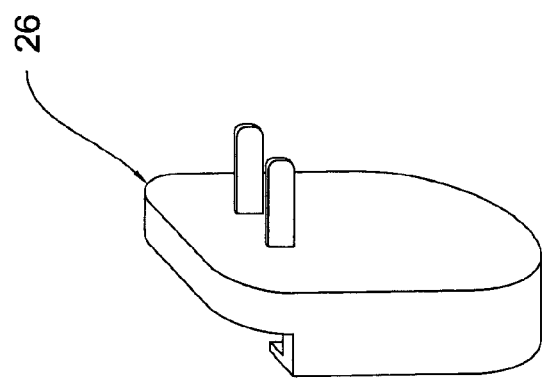
FIG. 9 is a perspective view illustrating an electrical air freshener embodiment of the rodent repellent system, constructed in accordance with the present invention, with a plug in component.
Figure 12:
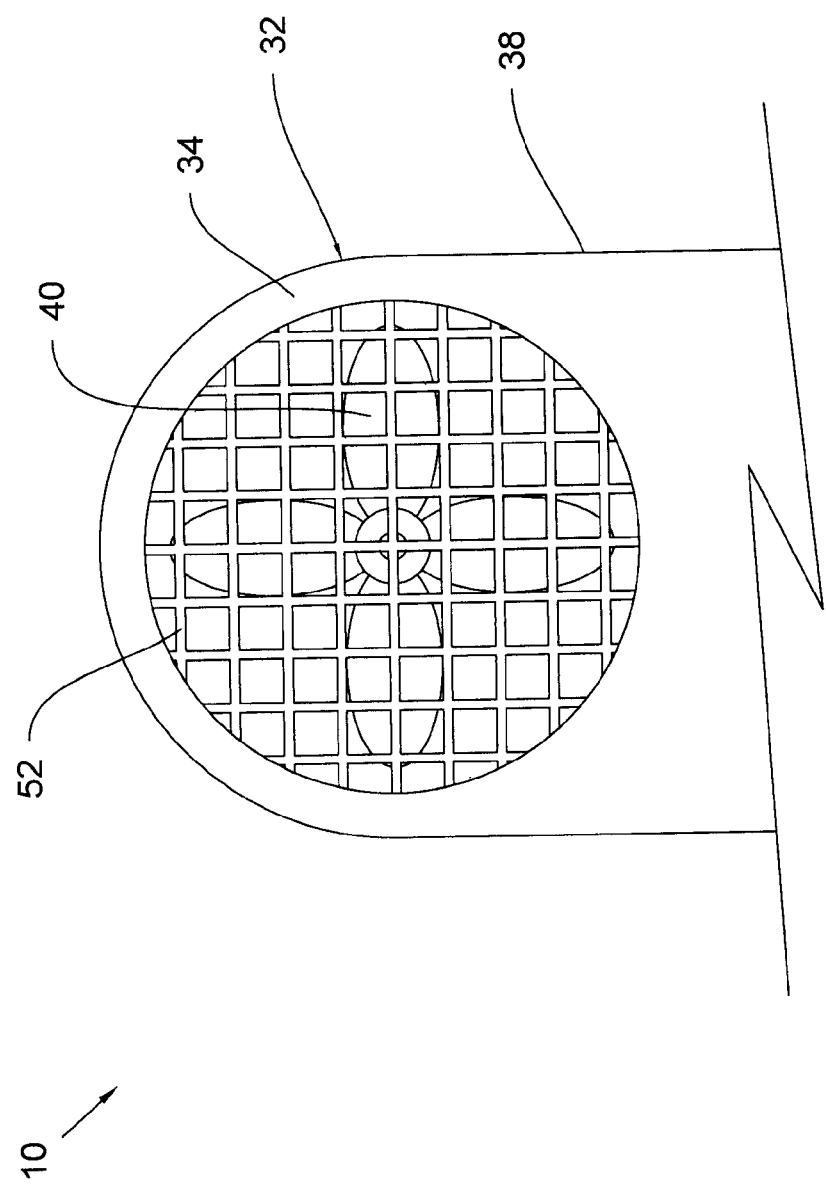
FIG. 12 is an elevational front view illustrating a fan housing of a fan dispersing apparatus embodiment of the rodent repellent system, constructed in accordance with the present invention.
Figure 17:
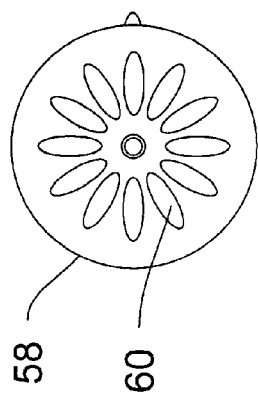
FIG. 17 is a top plan view illustrating an inner plate of the fan dispersing apparatus of the rodent repellent system of FIG. 12, constructed in accordance with the present invention, with the inner plate having a plurality of slots and/or apertures and movable relative to the fan dispersing apparatus.
Figure 18:
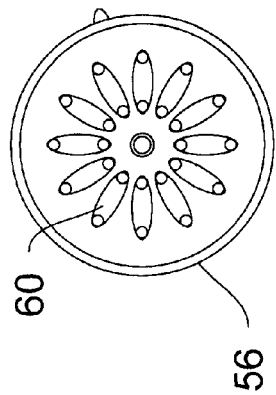
FIG. 18 is a top plan view illustrating a fixed plate of the fan dispersing apparatus of the rodent repellent system of FIG. 12, constructed in accordance with the present invention, with the fixed plate having a plurality of slots and/or apertures.
Figure 19:
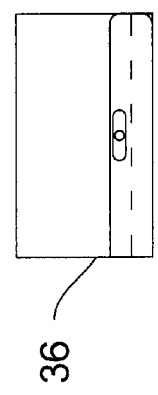
FIG. 19 is an elevational side view illustrating a dial type mechanism of the fan dispersing apparatus of the rodent repellent system of FIG. 12 of the rodent repellent system, constructed in accordance with the present invention, for adjusting the inner plate relative to the fixed plate.
Figure 16:
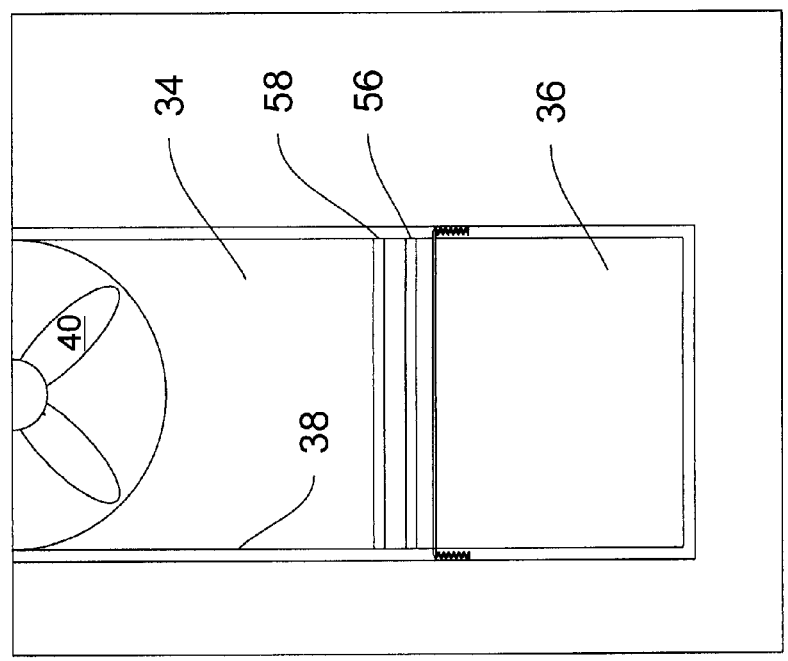
FIG. 16 is an elevational side view illustrating the concentrate housing and the fan housing of the fan dispersing apparatus embodiment of the rodent repellent system of FIG. 12, constructed in accordance with the present invention, with the concentrate housing threadably connected to the fan housing.

As best illustrated in FIGS. 9-11, the third embodiment of the Rodent Repellent System 10 of the present invention is an electric air freshener 26 configured to spread the scent of peppermint oil across a large room or open space. The electric air freshener 26 of the Rodent Repellent System 10 embodiment measures approximately two (2") inches in length by one half (½") inch in width and is small enough to fit into a wall outlet. Preferably constructed of hard plastic, the electric air freshener 26 includes a recessed housing 28 for storing a foam type mat 30 that contains peppermint oil. Occasionally, mat refills 30 are required for continual use. Electricity heats the peppermint oil contained in the included mat 30, allowing the scent to drift across a room.

The electric air freshener 26 of the Rodent Repellent System 10 of the present invention contains a variable speed motor that is user adjustable, allowing the user to decrease or increase the amount of dispersed scent throughout a room. Humans enjoy a pleasant mint smell in their immediate surroundings. Rodents find the scent overwhelmingly strong and unpleasant, and they run away from it. The electric air freshener 26 plugs into any standard wall outlet.

As illustrated in FIGS. 12-19, the fourth embodiment of the Rodent Repellent System 10 of the present invention is a fan dispersing apparatus 32 using a concentrate mixed with water, gel, or beads impregnated with a peppermint concentrate or formula. The fan dispersing apparatus 32 includes a fan housing 34 releasably secured to a concentrate housing 36. In a preferred embodiment, the fan housing 34 is threadably secured to the concentrate housing 36 although connecting the fan housing 34 to the concentrate housing 36 by other means is within the scope of the present invention.

The fan housing 34 of the fan dispersing apparatus 32 of the Rodent Repellent System 10 of the present invention includes an outer cover 38 with a fan 40 mounted within the outer cover 38. The fan 40 is preferably powered by a motor 42 positioned on a shelf 44 or the like within the outer cover 38 of the fan dispersing apparatus 32. The fan 40 can be powered by AC with a cord 46 extending from the motor 42 and through the outer cover 38 to be plugged into a standard wall outlet or can be powered with DC through a battery or other power source. An on/off switch 48 is provided on the outer cover 28 for activating and deactivating the fan motor 42, and thus the fan 40. A variable speed control 50 can also be provided allowing the user to adjust the speed of the fan 40. A screen 52 is positioned in an aperture formed in the outer cover 38 in front of the fan 40 allowing air to easily move from within the outer cover 34 to the area outside the outer cover 34.

As stated above, the concentrate housing 36 of the Rodent Repellent System 10 of the present invention is releasably secured to the outer cover 38 of the fan housing 34. In operation, prior to connecting the concentrate housing 36 to the fan housing 34, the concentrate housing 36 is sealed with a solid cover 54 such as aluminum foil or the like. Upon removal of the solid cover 54, the concentrate housing 36 is secured to the fan housing 34 allowing the peppermint to be in fluid communication with the fan 40. As the peppermint aroma fills the fan housing 34, it is dispersed from the fan housing 34 by the fan 40 and through the screen 52.

In order to regulate the amount of peppermint aroma filling the fan housing of the Rodent Repellent System 10 of the present invention, a fixed plate 56 and a movable inner plate 58 are provided between the fan housing 34 and the concentrate housing 36. Both the fixed plate 56 and the inner plate 58 have a plurality of slots and/or apertures 60 that overlap each other. By moving the inner plate 58 relative to the fixed plate 56, the size of the combined overlapping slots and/or apertures 60 change thereby controlling the amount of peppermint aroma leaving the concentrate housing 36 into the fan housing 34. Operation of the inner plate 58 can be accomplished by either rotating or sliding the inner plate 58 relative to the fixed plate 56. It is within the scope of the present invention to manipulate the inner plate 58 to actually close off all slots and/or apertures 60 thereby ceasing the flow of peppermint aroma escaping the concentrate housing 36.

With all embodiments, a possible formulation of the concentrate of the Rodent Repellent System 10 of the present invention includes 2% (0.50) oil of peppermint, 2% (0.50) oil of spearmint, 0.5% (0.10) camphor oil (optional), 1% (0.20) oil of cedar wood, and 1% (0.10) oil of lavender. If the formulations are not optimal for the particular rodent issue, the amount of peppermint and/or spearmint can be increased. Further, as will be understood by those persons skilled in the art, the formulations set forth above are merely an example and other formulations are within the scope of the present invention.

Figure 22:
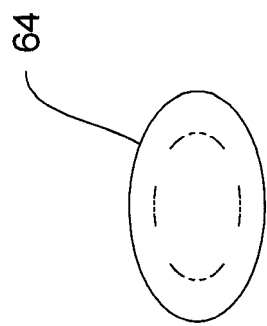
FIG. 22 is a top plan view illustrating a closable cover of the peppermint concentrate bottle of the rodent repellent system of FIG. 20, constructed in accordance with the present invention.
Figure 21:
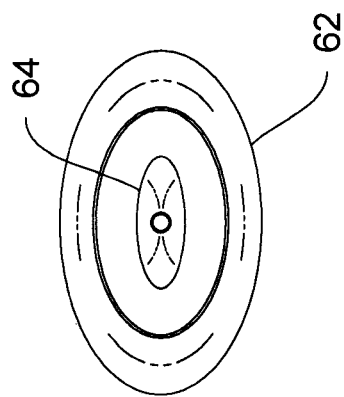
FIG. 21 is a top plan view illustrating the peppermint concentrate bottle of the rodent repellent system of FIG. 20, constructed in accordance with the present invention.
Figure 20:
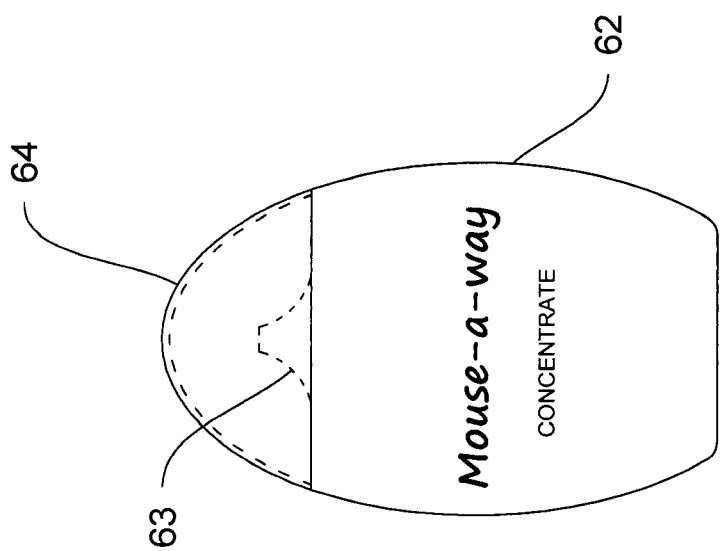
FIG. 20 is an elevational side view illustrating a peppermint concentrate bottle of the rodent repellent system, constructed in accordance with the present invention.

As best illustrated in FIGS. 20-22, the concentrate of the Rodent Repellent System 10 of the present invention can be provided in a bottle 62 with a dropper nozzle 63 covered with a cap 64. The concentrate within the bottle 62 can be added to water in a spray bottle or elsewhere or can be added to a gel material. In a preferred embodiment, an effective amount of the concentrate is six (6) to eight (8) drops per 32 ounces of water although other amounts are within the scope of the present invention.

Additional embodiments of the Rodent Repellent System 10 of the present invention include: a gel based canister; disposable wipes; electrical outlet plug-in unit with gel package insert; large size commercial size electric unit with fan and adjustable vent and speed motor; hand triggered sprayer with a separate concentrate in a dropper container to add water; electric wall plug-in unit for a wax melt with repellent wax melt cube, package to contain 10-12 sections, wherein the wax is melted by use of a halogen light as a heat source, this embodiment can be a stand alone unit or as a wall plug-in; candle; scented carpet powder; canister with gel beads and refill beads; gel beads that can be sprinkled on a plate and placed in basement or entry way that will dissipate in 30 to 45 days; a caulk and/or squeeze tube with repellant.

The electric air freshener and fan dispersing apparatus embodiments of the Rodent Repellent System 10 of the present invention effectively spreads the peppermint oil scent farther than the aforementioned embodiments, the gel based air freshener 12 and the surface wipes system 20. A user selects the necessary embodiment dependent on the space to be treated along with density amount and continuity of peppermint oil scent required in that space. All Rodent Repellent System 10 embodiments are highly effective and functional in both home residences and business establishments.

Although this invention has been described with respect to specific embodiments, it is not intended to be limited thereto and various modifications which will become apparent to the person of ordinary skill in the art are intended to fall within the spirit and scope of the invention as described herein taken in conjunction with the accompanying drawings and the appended claim.

The invention claimed is:

1. A rodent repellent system for repelling rodents from an area, the rodent repellent system consisting essentially of:
   a wiping cloth impregnated with peppermint oil, spearmint oil, camphor oil, cedarwood oil and lavender oil, wherein the wiping cloth is used to release oils into the area.

* * * * *